US00PP27901P2

(12) United States Plant Patent
Hansen

(10) Patent No.: US PP27,901 P2
(45) Date of Patent: Apr. 18, 2017

(54) ***HIBISCUS* PLANT NAMED 'STARRY STARRY NIGHT'**

(50) Latin Name: ***Hibiscus* hybrid (L.)**
Varietal Denomination: Starry Starry Night

(71) Applicant: Hans A. Hansen, Zeeland, MI (US)

(72) Inventor: Hans A. Hansen, Zeeland, MI (US)

(73) Assignee: Waltes Gardens, Inc., Zeeland, MI (US)

( * ) Notice: Subject to any disclaimer, the term of this patent is extended or adjusted under 35 U.S.C. 154(b) by 84 days.

(21) Appl. No.: 14/756,230

(22) Filed: Aug. 19, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Anne Grunberg

(57) ABSTRACT

A new and distinct cultivar of hardy herbaceous perennial *Hibiscus* hybrid plant named 'Starry Starry Night' comprising dense branching habit with dark greyed-purple, trifoliate leaves over a large portion of the mound. The flowers are flat, upward and outward facing, with pinwheel-varying light-pink and magenta colored face, veins and speckles, and have a darker red eye.

1 Drawing Sheet

Botanical classification: *Hibiscus* hybrid (L.).
Variety denomination: 'Starry Starry Night'.

BACKGROUND AND ORIGIN OF THE PLANT

The present invention relates to the new and distinct hardy, herbaceous, *hibiscus* plant, *Hibiscus* 'Starry Starry Night' hybridized by the inventor on Jul. 27, 2011 at a nursery in Zeeland, Mich. The new plant, originally labeled # 11-117-104, is a single seedling selection from a cross between *Hibiscus* 'Crown Jewels' U.S. Plant Pat. No. 11,857 (female pod parent) times *Hibiscus* 'Midnight Marvel' U.S. Plant Pat. No. 24,079 (male pollen parent). The seed was harvested on Nov. 11, 2011 the specific seedling passed the initial trial in the summer of 2012. Both parents have a complex mixture of species in them, most likely including the species: *moscheutos* and *coccineus*. *Hibiscus* 'Starry Starry Night' was first asexually propagated in 2013 by both stem tip cuttings and sterile tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Starry Starry Night' differs from its parents as well as all other hardy herbaceous *hibiscus* known to the applicant in many traits. The foliage color of 'Starry Starry Night' is very dark greyed-purple with generally tri-lobed foliage and occasional 5-lobed. The most similar *hibiscus* in flower color known to the applicant is 'Small Wonders' U.S. Plant Pat. No. 24,022, but the flower face of the new plant is flatter and not as cupped as 'Small Wonders' and the habit of the new plant is much larger mound. Other similar *hibiscus* include: 'Kopper King' U.S. Plant Pat. No. 10,793, 'Summer Storm' U.S. Plant Pat. No. 20,443, 'Cherry Cheesecake' U.S. Plant Pat. No. 26,089 and 'Turn of the Century' (not patented). 'Kopper King' has larger flowers, flowers for a shorter period, the petals have less veining, the foliage is not as dark, and the habit is larger and more open.

'Summer Storm' flowers for a longer period, the petals have less veining, and the habit is taller. 'Cherry Cheesecake' has petals with more folding along veins and more magenta tinting at petal apex rather than on the side of the petal. 'Turn of the Century' has more finely-dissected green foliage, smaller flowers with less veining and a more columnar plant habit with less branching. 'Starry Starry Night' has more foliage showing the darker greyed-purple coloration than all of the above cultivars and any cultivar known to the inventor.

Table 1 below shows further comparisons to similar cultivars.

TABLE 1

| CULTIVAR | Leaf color | Flower color | Habit | Size (H × W) |
|---|---|---|---|---|
| 'Cherry Cheesecake' | dark green with purple overtones | white, magenta tips, veins, and eye | upright mound | 145 cm × 140 cm |
| 'Mocha Moon' | deep bronze-green | white with scarlet eye | broad mound | 120 cm × 170 cm |
| 'Starry Starry Night' | dark greyed-purple | white and pink pinwheel, scarlet eye | mound | 120 cm × 120 cm |
| 'Summer Storm' | dark burgundy foliage | pink, rose veining, magenta eye | upright mound | 160 cm × 160 cm |
| 'Turn of the Century' | medium green | pink rose pinwheel, rose eye | upright mound | 120 cm × 110 cm |

*Hibiscus* 'Starry Starry Night' is a unique hardy herbaceous *hibiscus* with the following combined traits:

1. Hardy perennial producing herbaceous mound with dense branching;
2. Primarily tri-lobed foliage with very dark greyed-purple color over a large portion of the mound.
3. Many flowers up to 22 cm across over a prolonged season having a pinwheel-color effect of lighter pink on the exposed petal edge and becoming darker clock-wise toward the overlapped petal edge, accented by deep pink veining and a darker red lustrous eye.

4. Petals open to a flat face and recurve slightly toward apex.
5. Pink petal coloration toward apex in fine air-brushing-like spots.
6. Flowers self-cleaning leaving behind bright green calyx sharply contrasting with very dark foliage effect.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
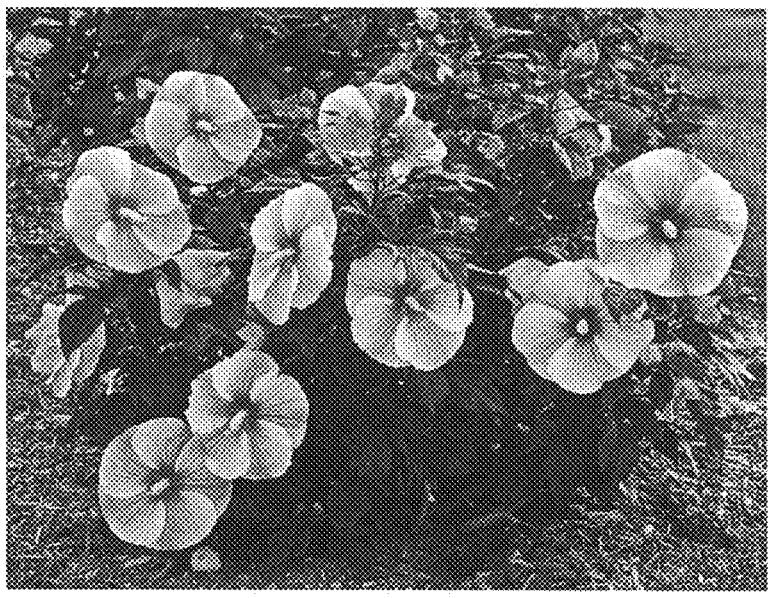
FIG. 1 shows a three-year old plant in the landscape in full-flower in August.
Figure 2:
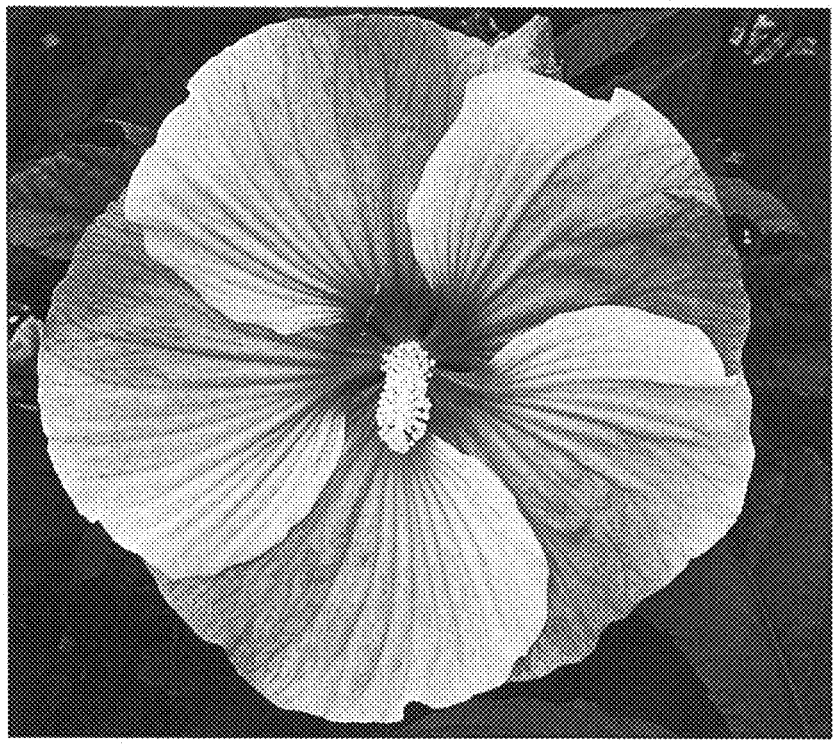
FIG. 2 shows a close-up of the flowers with intensely-veined and pinwheel-color effect.

The following descriptions and color references are based on the 2001 edition of The Royal Horticultural Society Colour Chart except where common dictionary terms are used. The new plant, *Hibiscus* 'Starry Starry Night', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand, open-field full-sun trials of a nursery in Zeeland, Mich. with supplemental fertilizer and water as needed. The plants are natural habit and were not treated with plant growth regulators, nor were they pinched at any time in the growth year.

Parentage: *Hibiscus* 'Crown Jewels' (female seed parent) times 'Midnight Marvel' (male pollen parent).

Propagation:

*Method*.—Stem cuttings and sterile plant tissue culture division.

*Time to initiate roots from tissue culture*.—About two weeks.

*Rooting habit*.—Normal, branching, developing thick to about 2.5 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant shape and habit*.—Hardy herbaceous perennial with 12 to 16 thick upright and heavily branched main stems producing a upright spreading mound about 100.0 cm tall and 147.0 cm wide, widest about 25 cm above soil line; 20 to 25 primary branches per main stem, lowest branches protruding at 10° above horizontal and curve upward to nearly 50°, upper branches straight 45° above horizontal; lowest branch about 28.0 cm long (shorter at the upper nodes) and 9.0 mm at base, decreasing in size distally.

*Stem*.—Rounded, glabrous, glaucous; average 92.0 cm tall and 2.0 cm diameter at base.

*Stem color*.—Lower region just above soil lighter than RHS 146D with heavy to solid tinting of nearest RHS 186C with glaucous covering and nearest RHS 185B with glaucous covering removed; in distal region or stem nearest RHS 187B without glaucous bloom to nearest RHS 185B with glaucous bloom.

*Plant size*.—Unpinched plant with stems about 100 cm tall; overall plant about 147 cm wide about 25 cm from the soil line (widest point).

*Internode*.—About 30 nodes per stem, average internode length about 3.3 cm of unpinched Plant.

Foliage description: Alternate; dentate; glabrous; predominately deeply cleft tri-lobed, rarely five-lobed; with side lobes at about 70 degree angle from center lobe; adaxial texture lustrous in distal leaves and matte in proximal leaves; abaxial texture matte; leaf blade size to about 19.5 cm long and about 18.0 cm across, average about 16.0 cm long and about 14.5 cm wide, smaller in distal portion of stem.

*Foliage color*.—Adaxial side of young expanding and mature leaves between RHS 187A and RHS N186A; abaxial side of young expanding and mature leaves nearest RHS 146B occasionally developing tinting of nearest RHS 187A.

*Veins*.—Palmate; adaxial primary and secondary between RHS 187B and RHS 187C on expanding and mature leaves, abaxial primary and secondary nearest RHS 183C toward leaf base and nearest RHS 183A toward apex.

*Petioles*.—Average size 8.5 cm long and 3.5 mm wide; mostly cylindrical with some flattening toward stem; slightly glaucous, glabrous.

*Petiole color*.—Adaxial nearest RHS 183B; abaxial between RHS 182A and RHS 182B.

Flower description:

*Buds*.—One day prior to opening about 7.0 cm long and 4.5 cm in diameter, acute apex and bluntly rounded base, unopened petals wrinkled at veins; ovoid with rounded apex, carinate at the sepal fusion seams.

*Bud color*.—Exposed petal color one day prior to opening between RHS 59D and RHS 63B toward apex and nearest RHS 62D toward base of flower with petal veins lighter than RHS 62D or N155D.

*Sepals*.—Five, proximal half connate forming campanulate star-shaped calyx; acute apex; margin entire, edentate; slightly puberulent; individually about 4.4 cm long, about 3.2 cm wide at fusion point and about 2.5 cm from fusion point to apex; forming a broad star about 2.0 cm deep and about 7.5 cm across.

*Sepal color*.—Adaxial between RHS 144A and RHS 146C; abaxial between RHS 144A and RHS 146C with tinting or blushing of nearest RHS 187B.

*Epicalyx*.—Linear, entire, puberulent, sharply acute apex and attenuate base, curved around sepals; typically 10 to 11 per flower; about 3.3 cm long tapering to base of about 5.0 mm wide.

*Epicalyx color*.—Adaxial and abaxial color nearest RHS 144A with apical tinting of between RHS 187A and RHS 187B.

*Flowers*.—Solitary, 60 to 72 per main stem without pinching including side branches; petals flattened in face; upward and outwardly facing; average about 23.0 cm across and about 6.0 cm deep from outside face to edge petals to center; size larger in early part of flowering season; persist for a one to two days; effective for at least 12 weeks beginning mid-July and lasting into October; no detectable fragrance.

*Petals*.—Five; glabrous, slightly lustrous in center and dull both front and back toward middle and perimeter, adnate to the androecium to form a column, imbricate to about 95% overlapping at widest part (petals nearly completely overlapping the next petal to the petal in the position two over), palmately veined, primary and secondary veins impressed on front and ribbed on back; shape: rounded; margins: entire, edentate; apex: rounded; base: short claw-like; size: average about 12.0 cm long and about 15.2 cm wide at widest portion (larger in earlier part of flowering season); center dark eye about 6.0 cm diameter.

*Petal color*.—Adaxial with lighter pink coloring on top petal side of lighter than RHS 62D or RHS 65D and darker on overlapped petal side and toward apex of between RHS 61C and RHS 61B; petals flecked or speckled with spots between RHS 61C and RHS 61B of about 1.0 mm long and 0.5 mm across and smaller; adaxial center nearest RHS 60A, veins radiating from center of nearest RHS 60A and becoming lighter toward apex; abaxial inner claw-like base 1.5 cm nearest RHS 155D, radiating toward apex from claw lighter than RHS 62D and developing tinting between RHS 61B and RHS 61C toward apex; abaxial veins nearest RHS 155D.

*Gynoecium*.—Style: enclosed in column about 6.5 cm long and about 1.0 cm wide at base; column puberulent; style puberulent; column color nearest RHS 158D; style protruding from column and split in distal 8.0 mm portion into typically five branches and protrudes from column, branch diameter 1.5 mm; branch color nearest RHS 158D; Stigma: typically five; globose, puberulose, about 3.5 mm in diameter; color nearest RHS 158D; Ovary: superior, about 1.2 mm across at base and 10.0 mm tall; acute apex; color nearest RHS 145C.

*Androecium*.—Filaments: numerous, about 150; less than 1.0 mm in diameter and about 6.0 mm long; attached along nearly the entire length of column; color nearest RHS 158D; Anthers: reniform; about 2 mm long and 1 mm wide; color nearest RHS 174D; Pollen: numerous, globose, less than 0.1 mm long, between RHS 158C and RHS 158B.

*Pedicel*.—Rounded in cross section, puberulent; length from base of sepal to abscission point average of about 2.8 cm long and about 4.0 mm wide, longer on early flowers decreasing in distal flowers.

*Pedicel color*.—Nearest RHS 138B.

*Peduncle*.—Rounded, puberulent, flowers are held easily visible on average about 6.5 cm long from abscission point to stem and about 3.0 mm wide, longer on earlier flowers.

*Peduncle color*.—Between RHS 182A and RHS 182B.

*Fruit*.—Few, loculicidal capsule; glabrous; globose, occasionally with abruptly acute apex; color between RHS N199B and RHS N199C when mature.

*Seed*.—Minutely floccose, typically globose; about 3.0 mm in diameter; color between RHS 200A and RHS N199B.

Resistance: *Hibiscus* 'Starry Starry Night' grows best with full sun and plenty of moisture, but can withstand some drought once established. Pest and disease resistance beyond that of other hardy perennial *hibiscus* cultivars has not been observed. Hardiness at least from USDA zone 4 through 9.

I claim:

1. A new cultivar of hardy herbaceous perennial *Hibiscus* hybrid plant named 'Starry Starry Night' as herein illustrated and described, suitable for potted plant culture, landscaping as a specimen or en masse, and especially suited for patios and confined spaces because of the compact habit.

* * * * *